United States Patent
Jansen et al.

(10) Patent No.: US 6,689,366 B1
(45) Date of Patent: Feb. 10, 2004

(54) SYNTHETIC VIRUS LIKE PARTICLES WITH HETEROLOGOUS EPITOPES

(75) Inventors: Kathrin U. Jansen, Doylestown, PA (US); Jessica C. Ling, Bensalem, PA (US); Steven W. Ludmerer, Piscataway, NJ (US); William L. McClements, Doylestown, PA (US); Xin-Min Wang, Schwenksville, PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/857,337

(22) PCT Filed: Dec. 14, 1999

(86) PCT No.: PCT/US99/29577

§ 371 (c)(1),
(2), (4) Date: Jun. 4, 2001

(87) PCT Pub. No.: WO00/35479

PCT Pub. Date: Jun. 22, 2000

Related U.S. Application Data

(60) Provisional application No. 60/112,610, filed on Dec. 17, 1998.

(51) Int. Cl.[7] .......................... C12N 15/37; C12N 15/85
(52) U.S. Cl. ................ 424/204.1; 424/192.1; 435/69.1; 435/69.3; 435/235.1
(58) Field of Search .................... 424/204.1, 178.1, 424/184.1, 205.1, 172.3, 192.1; 435/5, 235.1, 69.1, 69.3; 536/23.72; 514/2

(56) References Cited

U.S. PATENT DOCUMENTS

| 5,618,536 A | | 4/1997 | Lowy et al. |
| 5,738,853 A | * | 4/1998 | Ludmerer et al. ........ 424/204.1 |
| 5,795,754 A | * | 8/1998 | Ludmerer et al. ........ 435/172.3 |
| 5,821,087 A | * | 10/1998 | Lowe et al. ............... 435/69.3 |
| 5,922,588 A | | 7/1999 | Ludmerer et al. |
| 5,985,610 A | | 11/1999 | Lowy et al. |
| 6,013,262 A | | 1/2000 | Frazer et al. |

FOREIGN PATENT DOCUMENTS

WO    WO 97 18301    5/1997

OTHER PUBLICATIONS

Ludmerer, et al; Journal of Virology, vol. 70, No. 7, PP 4791–4794, 1996.
Ludmerer, et al; Journal of Virology, vol. 71, PP 3834–3839, 1997 224(2): 477–486, 1996.
Christensen, et al; Virology, 224(2): 477–486, 1996.

* cited by examiner

Primary Examiner—Laurie Scheiner
(74) Attorney, Agent, or Firm—Alysia A. Finnegan; Joanne M. Giesser

(57) ABSTRACT

The invention is a series of synthetic virus-like particles comprising a heterologous conformational epitope useful in the characterization of human papillomavirus infection, and useful to vaccinate individual for protection against HPV 6 and HPV 11 infections, and assays employing the synthetic virus-like particles.

2 Claims, 6 Drawing Sheets

```
                    6:28                    6:49-54
------------------------T--------------F---RA------         60
MWRPSDSTVYVPPPNPVSKVVATDAYV.RTNIFYHASSSRLLAVGHPY.SIK..NKTVVP
------------------------K--------------Y---KV------         60
                    11:28                    11:49-54

---------------------------------------------------F-        120
KVSGYQYRVFKVVLPDPNKFALPDSSLFDPTTQRLVWACTGLEVGRGQPLGVGVSGHP.L
---------------------------------------------------L-        120

6:169-178
----------S--------------------------------K--T--P--A-       179
NKYDDVENSG..GGNPGQDNRVNVGMDYKQTQLCMVGCAPPLGEHWGKG.QC.NT.VQ.G
----------GY-------------------------------T--S--S--N-       180
       11:132                                11:170-179

---------------------------------I-----T--------------       239
DCPPLELITSVIQDGDMVDTGFGAMNFADLQTNKSDVP.DICGT.CKYPDYLQMAADPYG
---------------------------------L-----V--------------       240

6:262-289
-----F-----------------E--------T-II--SG--T--G-----N------    299
DRLFF.LRKEQMFARHFFNRAG.VGEPVPD.L..KG..NR.SV.SSIYV.TPSGSLVSSE
-----Y-----------------T--------D-LV--GN--S--A-----H------    300
                         11:263-290
```

FIG.1A

```
                  6:324                     6:345-348
         -------------Q----------------------TT-S---------- 359
         AQLFNKPYWLQKAQGHNNGICWGN.LFVTVVDTTRSTNMTLCASV...S.TYTNSDYKEYM
         -------------H----------------------SK-A---------- 360
                  11:325                    11:346-349

-----Y-------------------------------------------- 419
         RHVEE.DLQFIFQLCSITLSAEVMAYIHTMNPSVLEDWNFGLSPPPNGTLEDTYRYVQSQ
         -----F-------------------------------------------- 420

6:433,438
         -------------P----NL-----------Y-------------S-I--V 479
         AITCQKPTPEKEK.DPYK..SFWEVNLKEKFSSELDQ.PLGRKFLLQSGYRGR.S.RTG.
         -------------Q----DM-----------F-------------T-A---I 480
              11:434,439

-------A-A------A---R                              500
         KRPAVSK.S.APKRKR.KTK.
         -------P-T------T---K                              501
```

FIG.1B

SEQUENCE LISTING

<160> NUMBER OF SEQ ID NOS: 1

<210> SEQ ID NO 1
<211> LENGTH: 462
<212> TYPE: PRT
<213> ORGANISM: Human papillomavirus

<400> SEQUENCE: 1

```
Met Trp Arg Pro Ser Asp Ser Thr Val Tyr Val Pro Pro Asn Pro
 1               5                  10                  15

Val Ser Lys Val Val Ala Thr Asp Ala Tyr Val Arg Thr Asn Ile Phe
                20                  25                  30

Tyr His Ala Ser Ser Arg Leu Leu Ala Val Gly His Pro Tyr Ser
        35                  40                  45

Ile Lys Asn Lys Thr Val Val Pro Lys Val Ser Gly Tyr Gln Tyr Arg
        50                  55                  60

Val Phe Lys Val Val Leu Pro Asp Pro Asn Lys Phe Ala Leu Pro Asp
65                  70                  75                  80

Ser Ser Leu Phe Asp Pro Thr Thr Gln Arg Leu Val Trp Ala Cys Thr
                85                  90                  95

Gly Leu Glu Val Gly Arg Gly Gln Pro Leu Gly Val Gly Val Ser Gly
                100                 105                 110

His Pro Leu Asn Lys Tyr Asp Asp Val Glu Asn Ser Gly Gly Gly Asn
                115                 120                 125

Pro Gly Gln Asp Asn Arg Val Asn Val Gly Met Asp Tyr Lys Gln Thr
                130                 135                 140

Gln Leu Cys Met Val Gly Cys Ala Pro Pro Leu Gly Glu His Trp Gly
145                 150                 155                 160

Lys Gly Gln Cys Asn Thr Val Gln Gly Asp Cys Pro Pro Leu Glu Leu
                165                 170                 175

Ile Thr Ser Val Ile Gln Asp Gly Asp Met Val Asp Thr Gly Phe Gly
                180                 185                 190

Ala Met Asn Phe Ala Asp Leu Gln Thr Asn Lys Ser Asp Val Pro Asp
                195                 200                 205

Ile Cys Gly Thr Cys Lys Tyr Pro Asp Tyr Leu Gln Met Ala Ala Asp
                210                 215                 220

Pro Tyr Gly Asp Arg Leu Phe Phe Leu Arg Lys Glu Gln Met Phe Ala
225                 230                 235                 240

Arg His Phe Phe Asn Arg Ala Gly Val Gly Glu Pro Val Pro Asp Leu
                245                 250                 255

Lys Gly Asn Arg Ser Val Ser Ser Ile Tyr Val Thr Pro Ser Gly Ser
                260                 265                 270

Leu Val Ser Ser Glu Ala Gln Leu Phe Asn Lys Pro Tyr Trp Leu Gln
                275                 280                 285

Lys Ala Gln Gly His Asn Asn Gly Ile Cys Trp Gly Asn Leu Phe Val
                290                 295                 300

Thr Val Val Asp Thr Thr Arg Ser Thr Asn Met Thr Leu Cys Ala Ser
305                 310                 315                 320

Val Ser Thr Tyr Thr Asn Ser Asp Tyr Lys Glu Tyr Met Arg His Val
                325                 330                 335

Glu Glu Asp Leu Gln Phe Ile Phe Gln Leu Cys Ser Ile Thr Leu Ser
                340                 345                 350
```

-continued

```
Ala Glu Val Met Ala Tyr Ile His Thr Met Asn Pro Ser Val Leu Glu
        355                 360                 365

Asp Trp Asn Phe Gly Leu Ser Pro Pro Pro Asn Gly Thr Leu Glu Asp
    370                 375                 380

Thr Tyr Arg Tyr Val Gln Ser Gln Ala Ile Thr Cys Gln Lys Pro Thr
385                 390                 395                 400

Pro Glu Lys Glu Lys Asp Pro Tyr Lys Ser Phe Trp Glu Val Asn Leu
                405                 410                 415

Lys Glu Lys Phe Ser Ser Glu Leu Asp Gln Pro Leu Gly Arg Lys Phe
            420                 425                 430

Leu Leu Gln Ser Gly Tyr Arg Gly Arg Ser Arg Thr Gly Lys Arg Pro
        435                 440                 445

Ala Val Ser Lys Ser Ala Pro Lys Arg Lys Arg Lys Thr Lys
    450                 455                 460
```

SYNTHETIC VIRUS LIKE PARTICLES WITH HETEROLOGOUS EPITOPES

This application is a 371 of PCT/US99/29577, filed Dec. 14, 1999. This application claims the benefit of provisional application No. 60/112,610 filed Dec. 17, 1998.

FIELD OF THE INVENTION

The present invention is directed to recombinant papillomavirus virus-like particles (VLPs) comprising heterologous neutralizing conformational epitopes. This invention also includes nucleic acids encoding these VLPs and assays employing these synthetic VLPs.

BACKGROUND OF THE INVENTION

Human papillomavirus (HPV) types 6 and 11 are the causative agents for more than 90% of all genital condyloma and laryngeal papillomas. HPV is a DNA virus which is enclosed in a capsid which is made up principally of L1 protein. The L1 proteins of HPV types 6 and 11 are very similar at both the amino acid and nucleotide level. Consequently, it has been difficult to develop assays which reliably distinguish between these two types of infection.

HPV 11 L1 residues $Gly^{131}$–$Tyr^{132}$ were previously identified as responsible for the type-specific binding of several HPV 11 neutralizing monoclonal antibodies (Ludmerer et al. 1996. "Two Amino Acid Residues Confer Type Specificity to a Neutralizing, Conformationally Dependent Epitope on Human Papillomavirus Type 11". *J. Virol.* 70:4791–4794). Within this same work, it was further demonstrated that a substitution at $Ser^{346}$ of the HPV 11 L1 sequence dramatically reduced binding of neutralizing monoclonal antibody H11.H3, and that the effect was specific for this antibody. Additional studies demonstrated that several HPV 11 neutralizing antibodies bound to a stretch of the HPV 11 L1 sequence between residues 120–140, whereas H11.H3 bound to a completely distinct site (Ludmerer et al. 1997. "A Neutralizing Epitope of Human Papillomavirus Type 11 is Principally Described by a Continuous Set of Residues Which Overlap a Distinct Linear, Surface-Exposed Epitope". *J. Virol.* 71:3834–3839).

However, these studies did not define which amino acid residues confer type specificity of binding for antibody H11.H3 completely. Furthermore, there may be other regions of HPV 11 VLPs, not described in these studies, which can elicit important HPV 11-specific, conformationally dependent responses. In addition, VLP-dependent antibodies specific for HPV 6 have also been generated (Christensen et al. 1996 "Monoclonal Antibodies to HPV-6 L1 Virus-Like Particles Identify Conformational and Linear Neutralizing Epitopes on HPV-11 in Addition to Type-Specific Epitopes on HPV-6". *Virology* 224(2):477–486). These antibodies could be useful in evaluation of infectivity by HPV 6. It would be desirable to determine the exact amino acids involved in the specificity of HPV type 6- and additional type 11-specific conformational epitope formations so that improved assays and vaccines may be developed.

DETAILED DESCRIPTION OF THE INVENTION

This invention is directed to a recombinant papillomavirus L1 protein of a first subtype which comprises a conformational epitope of a papillomavirus L1 protein of a second subtype. Preferably, the L1 protein is part of a virus-like particle (VLP). In some embodiments, the papillomavirus is a human papillomavirus (HPV). In a specific embodiment of this invention, a human papillomavirus L1 protein comprises a heterologous conformational epitope from HPV 6. In another specific embodiment of this invention, a human papillomavirus L1 protein comprises a heterologous conformation epitope from HPV 11.

Another aspect of this invention are nucleic acids encoding these heterologous L1 proteins, particularly DNA.

Another aspect of this invention are assays employing the synthetic virus-like particles.

Another aspect of this invention are vaccines comprising nucleic acids and/or proteins encoded by the nucleic acids, wherein the proteins comprise a heterologous conformational epitope.

BRIEF DESCRIPTION OF THE DRAWINGS

FIGS. 1A and 1B show the amino acid sequences for the L1 protein of HPV 6 and HPV 11 mutants utilized in these studies.

Figure 2A:
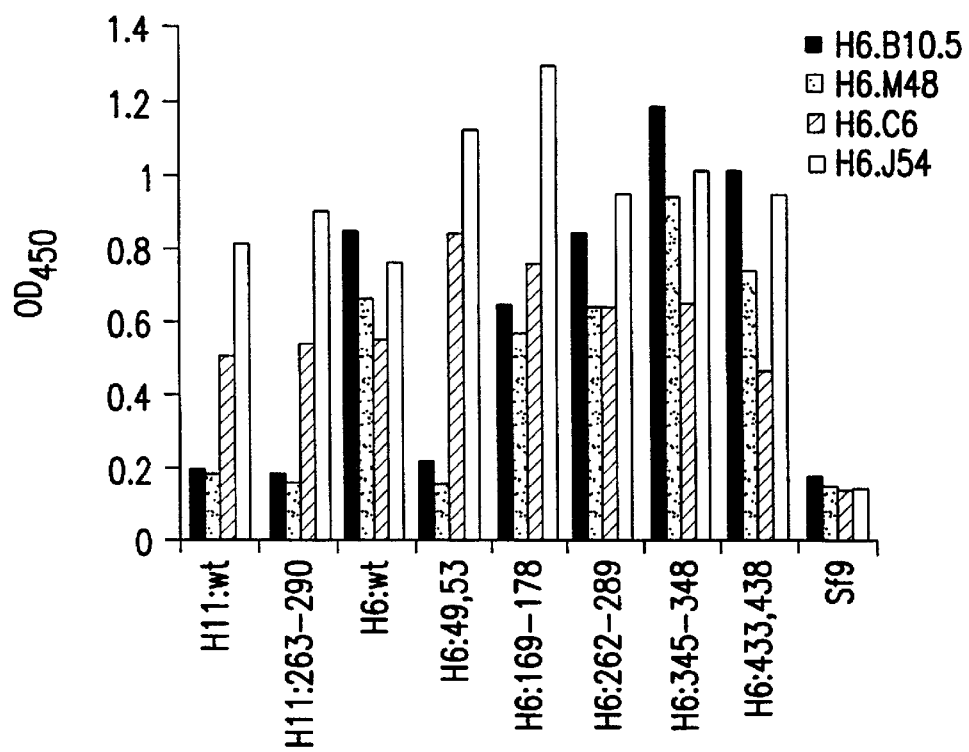
FIGS. 2A and 2B are graphs which show that amino acid substitutions at critical positions within the HPV 6 L1 sequence eliminate binding of monoclonal antibodies H6.B10.5, H6.M48, and H6.N8. In the first graph, the left most bar is H6.B10.5; the second bar is H6,.M48; the third bar is H6.C6 and the right most bar is H6.J54. In the second graph the left bar is H6.N8 and the right bar is H6.C6.
Figure 2B:
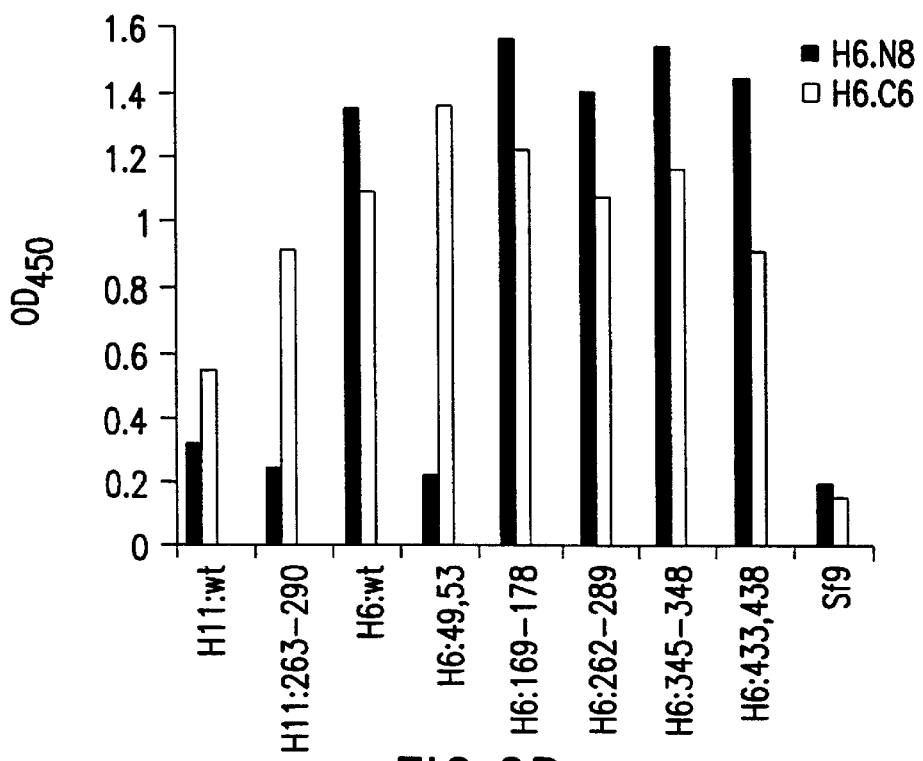
Figure 3:
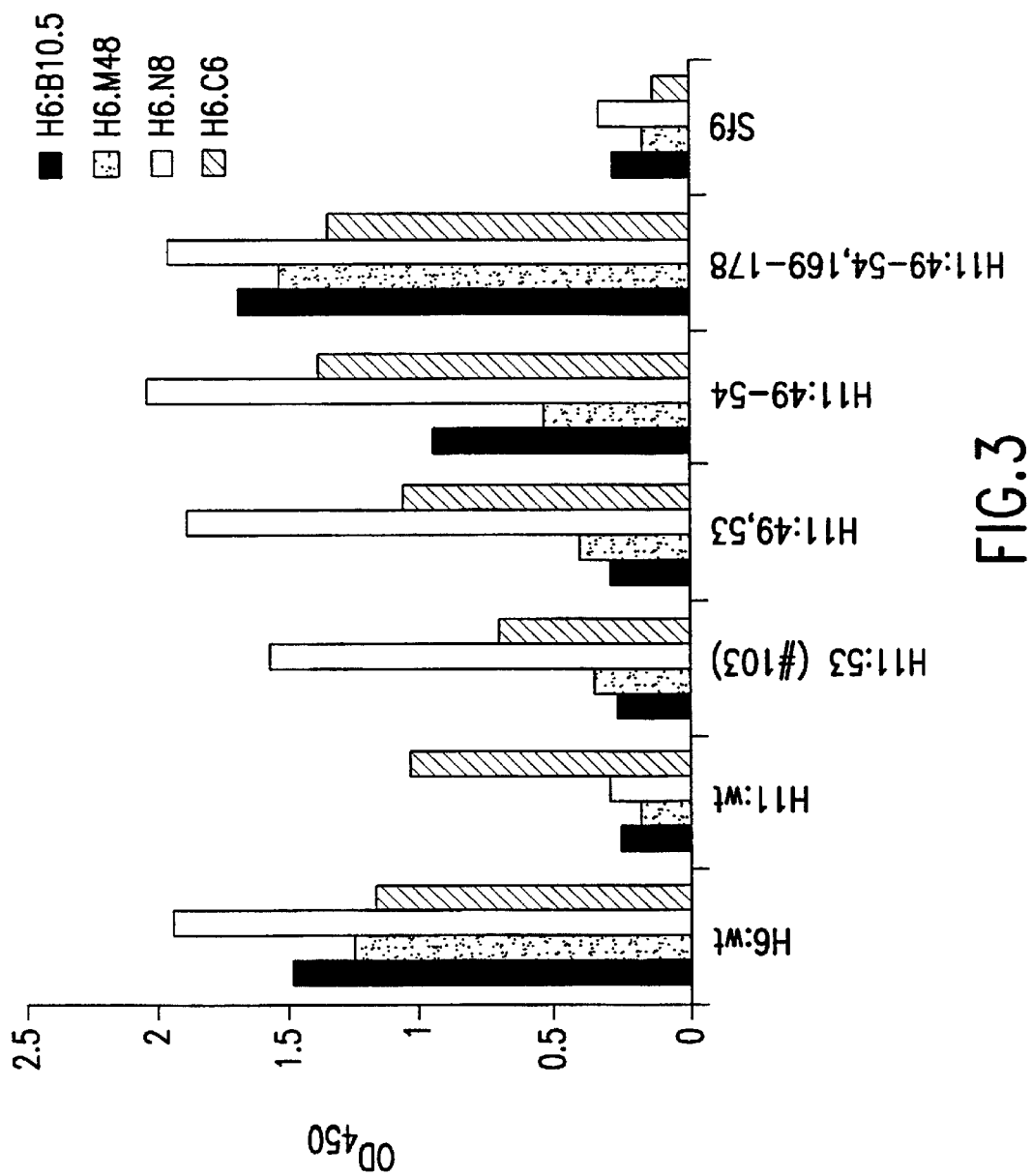
FIG. 3 shows substitutions into the HPV 11 L1 sequence which confer binding of HPV 6 specific monoclonal antibodies H6.B 10.5, H6.M48, and H6.N8. The left most bar is H6.B10.5; the next bar is H6.M48; the next bar is H6.N8 and the right most bar is H6.C6.
Figure 4:
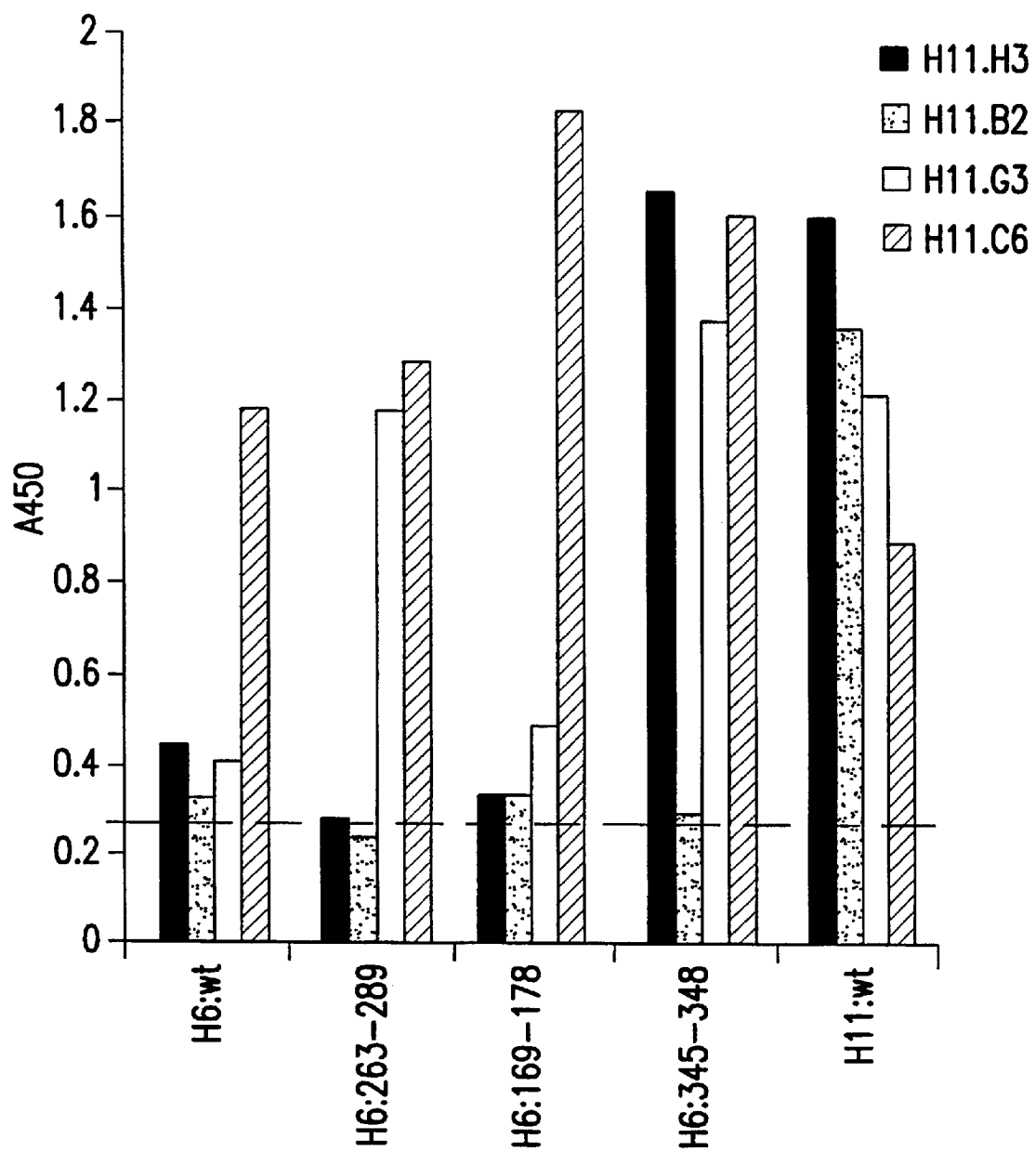
FIG. 4 shows that three amino acid substitutions into the HPV 6 L1 sequence between residues 345 and 348 confer binding of HPV 11 monoclonal antibodies H11.G3 and H11.H3. It also shows that seven substitutions between residues 262 and 289 also confer binding of HPV 11 monoclonal H11.G3. The left most bar is H11.H3; the second bar is H11.B2; the third bar is H11.G3; and the right most bar is H11.C6.
Figure 5:
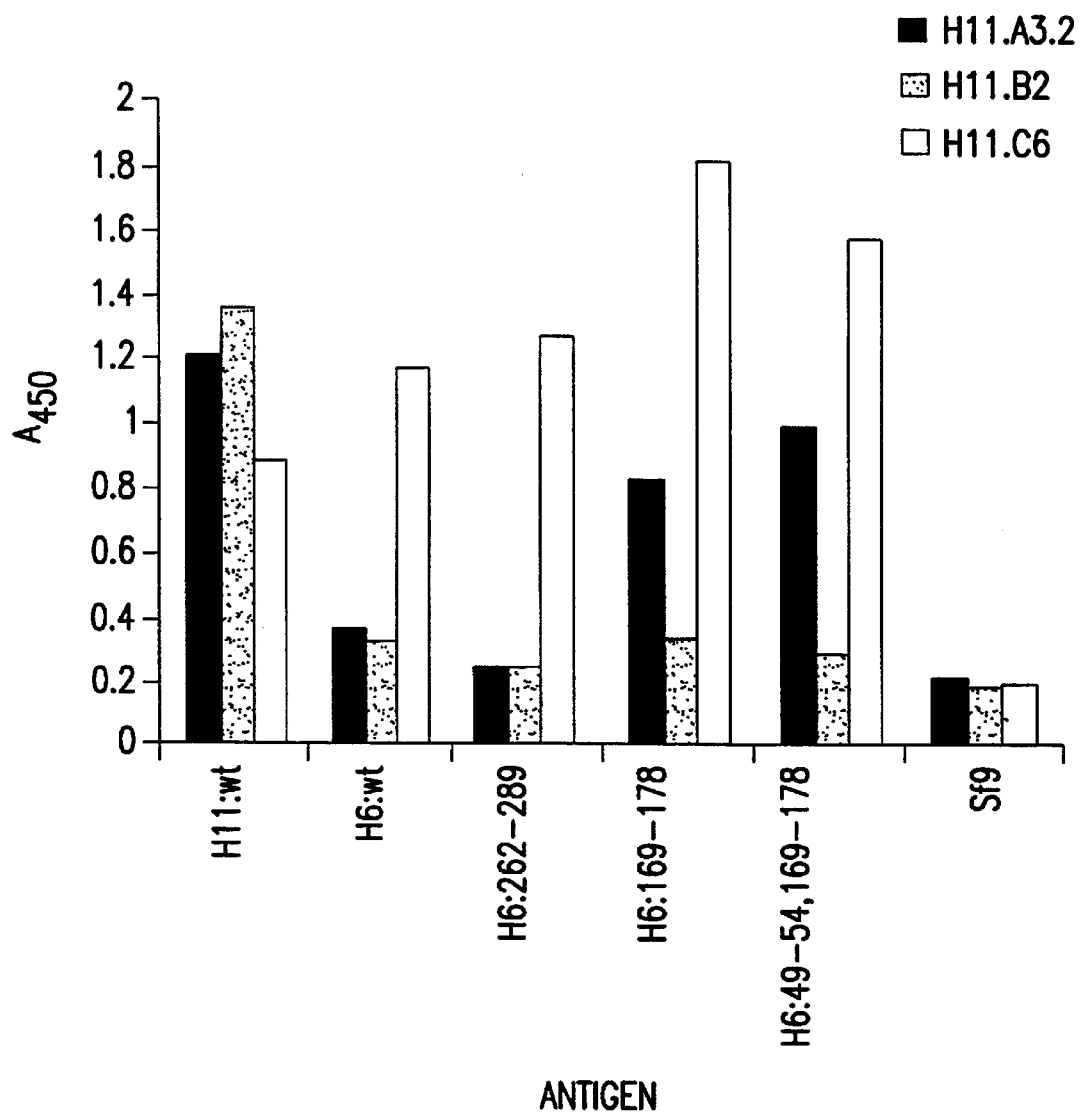
FIG. 5 shows that three substitutions into the HPV 6 sequence between residues 49 and 54, or four substitutions into the HPV 6 sequence between residues 169 and 178 confer binding of HPV 11 monoclonal antibody H11.A3.2. The left most bar is H11.A3.2; the middle bar is H11. B2 and the right bar is H11.C6.

As used throughout this specification and claims, amino acid residues (wild-type) are referred to by a two-part designation which is (i) the one-letter standard amino acid abbreviation of the wild-type residue, followed by (ii) the position of the amino acid in the L1 protein. Residues specified in this format would also be for a particular HPV type. For example, "HPV 6 K53" means the lysine residue at position 53 of HPV 6 L1.

As used throughout this specification and claims, mutated amino acids are referred to by a three-part designation which is (i) the one-letter standard amino acid abbreviation of the wild-type amino acid (ii) the position of the amino acid in the L1 protein of a particular HPV type, and (iii) the one letter abbreviation for the amino acid which is now present. For example, HPV 6 "T345S " means that the threonine residue, normally present at position 345 of HPV 6 L1, has been changed to serine.

Monoclonal antibodies referred to throughout this specification are listed below (all were obtained from Dr. Neil Christensen of Pennsylvania State University, Hershey, Pa.).

H6.B10.5—this antibody is specific to HPV 6 L1 protein in VLPs.

H6.M48—this antibody is similar to H6.B10.5 in that it binds to HPV 6 L1 protein in VLPs.

H6.N8—this antibody is similar to H6.B 10.5 in that it binds to HPV 6 L1 protein in VLPs.

H11.G3—this antibody is specific for HPV 11 VLPs and its binding is conformationally dependent.

H11.H3—this antibody is specific for HPV 11 VLPs, and is neutralizing. It is known that HPV 11 L1 residue S346 is critically important for the binding of H11.H3, and that a substitution at this position does not affect binding of HPV 11-specific VLP-dependent antibodies demonstrated to bind elsewhere.

H6.J54—this antibody binds VLPs of both HPV 6 and HPV 11, but not other HPV types.

H6.C6—this antibody binds both HPV 6 and 11 VLPs; it also binds both native and denatured material. It can be used to determine total L1 production.

H11.A3—this antibody specifically binds HPV 11 VLPs, but at a different region than either H11.B2 or H11.H3.

H11.B2—similar to H11.A3 in that it specifically binds HPV 11 VLPs, but at a different region than either HI11.H3 or H11.A3.

In order to develop an assay which would distinguish between HPV 6 and HPV 11 responses, the amino acids residues that confer antigenic type-specificity on HPV subtypes had to be determined. Therefore we focused on regions of HPV 6 which have multiple divergences from HPV 11 within a short stretch. To streamline the process of analyses, mutants of HPV 6 which were multiply mutated at these regions were synthesized and the VLPs produced from them were analyzed for effects on antibody binding.

In order to construct the VLPs of this invention, the amino acid residues which make up the conformational epitopes where type specific, VLP-dependent monoclonal antibodies bind had to be determined. This was accomplished by mapping the binding sites of monoclonal antibodies which bind specifically to either HPV 6 or HPV 11 VLPs. L1 of either HPV 6 or HPV 11 was modified by introducing amino acid substitutions at various positions, then determining if the mutant protein would bind either HPV 6- or HPV 11-specific monoclonal antibodies. Mapping was confirmed by demonstrating transfer of binding of a monoclonal to one of these types to the other type which had been minimally modified. Modified VLPs used for these transfers were demonstrated to retain binding of other type-specific antibodies.

In accordance with this invention it has been found that HPV 6 L1 with three HPV 11 L 1-like substitutions, at T345, T346 and S348 produce VLPs that bind HPV 11-specific monoclonal antibodies H11.G3 and H11.H3. These two antibodies can be distinguished in that H11.G3, but not H11.H3, can also bind HPV 6 VLPs which contain seven substitutions between residues 262 and 290. In specific embodiments of this invention, the substitutions are T345S, T346K, and S348A.

Furthermore, we show that HPV 6 L1 with either three HPV 11 L 1-like substitutions between amino acids 49 and 54 (at F49, R53, and A54), or four HPV 11 L1-like substitutions between residues 169 and 178 (at K169, T172, P175, and A178), can bind HPV 11-specific, VLP dependent monoclonal antibody H11.A3.2. In specific embodiments of these class of mutants, the substitutions are (i) the combination of F49Y, R53K, and A54V; and (ii) K169T, T172S, P175S, and A178N.

Thus one aspect of this invention is a recombinant HPV 6 L1 protein which also presents a major neutralizing, conformational epitope of HPV 11. In a preferred embodiment, the conformational epitope comprises T345S, T346K and S348A. These whole regions may be transferred to other HPV types through alignment, generating more refined tools for serological analysis. Thus this invention comprises any papillomavirus type which comprises a heterologous neutralizing conformational epitope of HPV 11 mapped in these studies.

This invention also includes HPV 6 L1 proteins with HPV 11-like substitutions between residues 49–54, 169–178, and 261–290, specifically at (i) F49, R53, and A54; (ii) K169, T273, P175 and A178; and (iii) E262, T270, S276, G277, T280, G283, and N289. In specific embodiments of this class of mutants, the substitutions are: (i) F49Y, R53K, and A54V; (ii) K169T, T273S, P175S, and A178N; and (iii), E262T, T270D, S276G, G277N, T280S, G283A, and N289H. These portions of the protein comprise part of the epitope for HPV 11-specific VLP dependent monoclonal antibodies H11.A3.2, and H11.G3.

A further aspect of this invention is nucleic acids encoding the L1 proteins comprising the heterologous conformational epitopes discussed above, including HPV 11conformational epitope T345S, T346K and S348A. As L1 protein and nucleic acid sequences are generally well known, it is within the skill of the ordinary artisian to insert the mutations described herein using conventional genetic engineering/protein engineering techniques. In a preferred embodiment the nucleic acid is a DNA, and codons may be optimized for increased viral expression for a given host cell.

Other aspects of this invention include vectors such as plasmids which contain the nucleic acids encoding L1 proteins comprising a heterologous HPV 11 conformational epitope. Also included in this invention are host cells, particularly yeast, bacterial, insect, and mammalian cells containing a nucleic acid encoding an L1 protein comprising an HPV 11 conformational epitope, whether or not present in a vector.

In another aspect of this invention, HPV 6 epitopes were transferred to HPV 11. In this embodiment, HPV 11 L1 modified with either one (at K53) or two (at Y49 and K53) substitutions show approximately a 10-fold increase in binding of HPV 6-specific monoclonal antibody H6.N8. In the case of H6.N8, the level of binding was comparable to that observed with prototype HPV 6 VLPs. This demonstrates that part of the epitope, including its type 6 specificity, is defined by these and neighboring residues. Preferred substitutions are K53R, and the combinantion of Y49F and K53R.

Another HPV 11 heterologous L1 protein comprises three changes: at Y49, K53, and V54. HPV 11 L1 modified with these three changes show approximately four-fold binding above background to HPV 6-specific monoclonal antibodies H6.B10.5 and H6.M48, in addition to binding monoclonal antibody H6.N8 as discussed above. In specific embodiments of this class of mutants, the substitutions are Y49F, K53R, and V54A.

Another HPV 11 L1 mutant encompasses seven changes in two regions (49–54 and 170–179). These changes are at positions Y49, K53, V54, T170, S173, S176, and N179. HPV 11 L1 modified with these seven substitutions show binding to antibodies H6.B10.5, H6.M48, and H6.N8 comparable to that observed with prototype HPV 6 VLPs. These HPV 6 epitopes can be moved to any desired PV type. In preferred embodiments the substitutions are HPV 6 residues F49, R53, A54, K169, T172, P175, and A178, placed into equivalent positions of the selected PV L1 type by alignment.

Another aspect of this invention is nucleic acids encoding the L1 proteins comprising a heterologous conformational epitope, including (i) HPV 6 conformational epitope K53R, (iv) the combination of Y49F and K53R, (iii) the combination of Y49F, K53R, and V54A, (iv) the combination of Y49F, K53R, V54A, T170K, S173T, S276P and N179A; and (v) combinations of (i), (ii), (iii) and/or (iv). As L1 protein and nucleic acid sequences are generally well known, it is within the skill of the ordinary artisan to insert the mutations described herein using conventional genetic engineering/ protein engineering techniques. In a preferred embodiment the nucleic acid is a DNA, and codons may be optimized for increased viral expression for a given host cell. Other aspects of this invention include vectors such as plasmids which contain the nucleic acids encoding L1 proteins comprising a heterologous HPV 6 conformational epitope. Also included in this invention are host cells, particularly yeast, bacterial, insect, and mammalian cells containing a nucleic acid encoding an L1 protein comprising an HPV 6 conformational epitope, whether or not present in a vector.

In another aspect of this invention is the transfer of conformational epitopes to a more distantly-related PV type. Almost every species of animal studied to date has a PV, including cottontail rabbit, bovine, canine, and the like. This discussion and the examples focus on the use of cottontail rabbit papillomavirus (CRPV) comprising heterologous conformational epitopes to produce serological reagents of higher specificity to monitor HPV 6 and HPV 11 responses and infectivity. However, it is intended that any PV can substitute for CRPV for these uses, and the present invention is specifically directed to this broad usage. Thus, this invention specifically includes a recombinant CRPV L1 protein comprising at least one heterologous conformational epitope. In specific embodiments, the heterologous conformational epitope is selected from the groups consisting of human HPV 6 and HPV 11 epitopes, and placed into CRPV L1 by amino acid alignment. This invention also includes nucleic acids encoding the recombinant protein, vectors comprising the nucleic acids, and host cells which comprise the vectors.

A further aspect of the invention is the generation of VLPs which can elicit both HPV 6 and HPV 11 responses. HPV 6 VLPs which contain HPV 11 substitutions T345S, T346K, and S348A will present a major HPV 11 neutralizing epitope alongside all HPV 6 responses. HPV 11 VLPs modified to contain HPV 6 substitutions, such as the combination of Y49F and K53R; the combination of Y49F, K53R, and V54A; or the combinantion of Y49F, K53R, V54A, T170K, S173T, S 176P and N179A will present the one known HPV 6 specific conformational epitope alongside most HPV 11 epitopes, including the major neutralizing epitopes. The latter is significant in that all known neutralizing epitopes are conformationally dependent, and conformational dependence is believed to be a necessary property of such epitopes.

Because of the high identity between wild-type HPV 6 and HPV 11 L1 sequences, present serological assays cannot distinguish responses between these two types very well. The modified VLPs of this invention will identify HPV 6 and HPV 11 immune responses upon infectivity or immunization. VLPs which elicit neutralizing responses to both types can simplify vaccine manufacturing, and lower costs for the consumer.

Another aspect of this invention is the use of these derivatized HPV 6 and HPV 11 VLPs as reagents in serological assays. Because most epitopes are shared between HPV 6 and HPV 11 VLPs, polyclonal sera to one competes with the binding of a type-specific monoclonal antibody to the other due to steric hindrance from the binding of antibodies to neighboring sites. In accordance with this invention, HPV 6 and HPV 11 epitopes can be moved to a more distant VLP type, such as CRPV, where there are no cross-reactive epitopes between CRPV and either HPV 6 or HPV 11. Therefore, presentation of HPV 6- and HPV 11-specific epitopes on a CRPV VLP eliminates the problem of steric competition from neighboring epitopes. Only the presence of antibody in a polyclonal response to the specifically transferred epitope should compete with monoclonal antibody binding.

One assay of this invention distinguishes between the presence of HPV 6 and HPV 11 antibodies in a sample suspected of containing either or both types of antibodies comprising the steps of:

a) contacting the sample with recombinant PV protein comprising either a heterologous HPV conformational epitope or a heterologous HPV 11 conformational epitope; and b) detecting binding between the antibodies present in the sample and the recombinant PV protein;

wherein binding to a heterologous HPV 11 conformational epitope indicates the presence of HPV 11 antibodies in the sample, and binding to a HPV 6 conformational epitope indicates the presence of HPV 6 antibodies in the sample.

Yet another aspect of this invention comprises an assay for discrimination between HPV 6 and HPV 11 in a subject suspected of being infected with either HPV 6 or HPV 11, or vaccinated for protection against HPV 6 and/or HPV 11 infection, comprising the steps of:

a) obtaining a blood sample from the subject, wherein said blood sample comprises either HPV 6 or HPV 11 antibodies;

b) contacting the sample with a recombinant VLP comprising either a heterologous HPV 6 conformational epitope or a heterologous HPV 11 conformational epitope; and c) detecting binding between the antibodies present in the sample and the heterologous VLP;

wherein binding a VLP comprising a heterologous HPV 11 conformational epitope indicates an HPV 11 infection, and binding to a VLP comprising a heterologous HPV 6 conformational epitope indicates an HPV 6 infection. In preferred embodiments, the VLP is from a distantly related PV, such as a CRPV VLP.

Another aspect of this invention are vaccines which comprise either L1 protein comprising a heterologous conformational epitope, or the nucleic acid which encode these proteins. In specific embodiments, the protein comprises both an HPV 6 and an HPV 11 epitope; either or both may be heterologous. This vaccine will confer protection against both types of HPV infection, as neutralizing antibodies to both viral epitopes are produced. The protein-based vaccine may be formulated according to conventional vaccine formulation techniques, and include such well known, traditional components as adjuvants, and pharmaceutically acceptable carriers. This vaccine may be administered intranasally, intravenously, intramuscularly, or subcutaneously, either with or without a booster dose. Likewise, nucleic-acid based vaccines, or specifically, DNA vaccines may be similarly formulated and administered.

The following examples are provided to further define the invention without however, limiting the invention to the particulars of these examples.

EXAMPLE 1

Generation of Test Expression Constructs

The HPV 6 and HPV 11 L1 structural genes were cloned from clinical isolates using PCR with primers designed from the published L1 sequence. The L1 genes subsequently were subcloned both into BlueScript (Pharmacia) for mutagenesis, and pVL1393 (Stratagene) for expression in Sf9 cells.

Mutations were introduced into the L1 gene using Amersham Sculptor in vitro mutagenesis kit according to the manufacturer's recommendations. The appearance of the desired mutation was confirmed by sequencing, and the mutated gene subcloned into pVL1393 for expression in Sf9 cells.

EXAMPLE 2

Transient Expression of L1 VLPs in SF9 Cells

SF9 cells were transfected using BaculoGold Transfection kit (Pharmringen). Transfections were done essentially according to the manufacturer's instructions with the following modifications. $8 \times 10^8$ Sf9 cells were transfected in a 100 mM dish, with 4 μg of BaculoGold DNA and 6 μg of test DNA. Cells were harvested after 6 days and assayed for VLP production.

EXAMPLE 3

Preparation of SF9 Extracts and ELISA Assays

Cells were harvested six days after transfection, by scraping followed by low speed centrifugation. Cells were resuspended in 300 ml of breaking buffer (1 M NaCl, 0.2 M Tris pH 7.6) and homogenized for 30 minutes on ice using a Polytron PT 1200 B with a PT-DA 1205/2-A probe (Brinkman) in a Falcon 1259 tube. Samples were spun at 2500 rpm for 3 minutes to pellet debris. Tubes were washed with an additional 150 ml of breaking buffer, supernatants collected in a 1.5 ml microfuge tube, and respun for 5 minutes in an Eppendorf microfuge (Brinkman). Supernatants were collected and stored at 4° C. until use. ELISA assays typically were performed the same day, although samples may be frozen on dry ice, stored at −80° C., thawed and assayed at convenience.

5 ml of extract was diluted into 50 ml of 1% BSA in PBS (phosphate buffered saline; 20 mM $NaPO_4$, pH 7.0, 150 mM NaCl) and plated onto a polystyrene plate. The plate was incubated overnight at 4° C. Extracts were removed and the plate blocked with 5% powdered milk in PBS. All subsequent wash steps were performed with 1% BSA in PBS. The plate was incubated at room temperature with primary antibody for 1 hour. Primary antibodies (monoclonal antibodies generated against HPV 11 virions, HPV 11 VLPs, or HPV 6 VLPs) were obtained as ascites stock from Dr. Neil Christensen (Pennsylvania State University). They were diluted $10^5$-fold in 1% BSA PBS before use. After washing, plates were incubated for 1 hour with secondary antibody. The secondary antibody, peroxidase labeled Goat anti-Mouse IgG (γ), was purchased from Kirkegaard & Perry Laboratories, Inc. and used at $10^3$ dilution in 1% BSA in PBS. After a final washing, a horse radish peroxidase assay was performed and absorbance read at 450 nm.

EXAMPLE 4

Two Near Adjacent Substitutions Into the HPV 6 L1 Sequence Eliminates Binding of HPV 6-Specific, VLP-Dependent Monoclonal Antibodies We predicted that an HPV 6-specific monoclonal antibody (one which does not bind to closely related HPV 11 VLPs) would bind a region where there are several adjacent or near adjacent residues between types 6 and 11 L1 genes. Excluding the C-terminus (it has been shown that the C-terminus is non-essential for VLP formation), there are five such regions. Using standard procedures, we generated test clones which had multiple 11-like substitutions in each of these five regions. Only clone 1393:6:49–53, which harbors substitutions at L1 residues 49 and 53 (F49Y, R53K) produced VLPs which had an effect on H6.B10.5, H6.M48, and H6.N8 binding. Binding of HPV 11-cross-reactive antibody H6.J54, also VLP-dependent, was not disturbed, demonstrating the presence of VLPs.

EXAMPLE 5

Transfer of Binding of H6.B10.5, H6.M48 and H6.N8 to modified HPV 11 VLPs

Based upon the studies in Example 4, we generated mutants of HPV 11 L1 with HPV 6-like substitutions at positions within the first 60 residues where the two L1 sequences differ. We also generated HPV 11 mutants with single substitutions at either Y49F or K53R. A third HPV 11 clone harbored three HPV 6-like substitutions between residues 49 to 54 (Y49F, K53R, and V54A), and a fourth clone harbored three HPV 6-like substitutions between residues 49 to 54 and 4 substitutions between residues 170 to 180 (Y49F, K53R, V54A and T170K, S173T, S176P, N179A).

Clones 1393:11:K53R and 1393:11:Y49F,K53R both generated VLPs which produced approximately ten-fold binding above background of HPV 6-specific monoclonal antibody H6.N8. An additional clone, 1393:11:Y49F,K53R, V54A, generated VLPs which showed approximately four-fold binding above background of monoclonal antibodies H6.B10.5 and H6.M48.

Antibody H6.C6 is cross-reactive between types 6 and 11 L1, and binds both native and denatured material. Thus it is a measure of total L1 production. Normalized to L1 production, the level of H6.N8 binding was comparable to that observed with prototype HPV 6 VLPs. VLPs produced from clone 1393:11:49–54,170–180, which harbored seven HPV 6-like substitutions over two distinct areas of L1 (Y49F, K53R, V54V; and T170K, S173T, S176P, N179A) showed a level of binding to antibodies H6.B10.5, H6.M48, and H6.N8 which was comparable to that observed with prototype HPV 6 VLPs.

Antibodies H11. B2 and H11.H3, both type 11-specific and VLP-dependent, are known to bind other regions of the L1 sequence. Hence these substitutions at the N-terminus should not impact their binding. They bound these N-terminally mutated constructs, thus demonstrating that these N-terminal substitutions had no effect on VLP assembly, or on the presentation of critical HPV 11 neutralizing epitopes.

This result is especially significant in light of the fact that the binding site of antibody H11 .B2 previously was mapped to a stretch of residues between Y123 and V142, a region which lies in between the two multiply mutated regions discussed in the present example. This demonstrates that the structural perturbations generated by the mutations discussed in this work are quite localized.

EXAMPLE 6

Three substitutions Into HPV 6 L1 Sequence Confer H11.G3 and H11.H3 Binding

HPV 6 L1 was modified with HPV 11-like substitutions to generate 1393:6:T345S,T346K, and A348S. This clone was expressed transiently in Sf9 cells, and VLPs were produced and tested for binding for both antibodies H11.G3 and H11.H3. We observed binding 10-fold above background levels, commensurate with binding to prototype HPV 11 VLPs. Binding of HPV 6-specific antibodies H6.B10.5 and H6.M48 was not perturbed, demonstrating that the VLPs retained HPV 6-like character. Furthermore, binding of HPV 11-specific antibodies H11 .A3 and H11. B2, antibodies known to bind elsewhere, was not observed, thus demonstrating that the transfer was specific to H11.G3 and H11.H3.

EXAMPLE 7

Seven Substitutions Into HPV 6 L1 Sequence Confer H11.G3 Binding

HPV 6 L1 was modified with seven HPV 11-like substitutions between residues 262 and 289 (E262T, T270D, S276G, G277N, T280S, G283A, N289H) to generate clone 1393:6:262–289. This clone was expressed transiently in Sf9 cells, and VLPs were produced and tested for binding. We observed binding 10-fold above background levels of antibody H11.G3. Binding of HPV 6 specific antibodies H6.B10.5 and H6.M48 was not perturbed, demonstrating that the VLPs retained HPV 6-like character. Furthermore, binding of HPV 11-specific antibodies H11.A3 and H11.B2, antibodies known to bind elsewhere, was not observed, thus demonstrating that the transfer was specific to H11.G3.

EXAMPLE 8

Three Substitutions Into HPV 6 L1 Sequence Between Residues 49 and 54, or Four Substitutions Between Residues 169 and 178, Confer H11.A3.2 Binding HPV 6 L1 was modified with three HPV 11-like substitutions between residues 49 and 54 (F49Y, R53K, and A54V and four HPV 11-like substitutions between residues 169 and 178 (K169T, T172S, P175S, and A 178N), or four HPV 11-like substitutions between residues 169 and 178 (K169T, T172S, P175S, and A178N) to generate clones 1393:6:49–54,169–178 and 1393:6:169–178 respectively. These clones were expressed transiently in Sf9 cells, and VLPs were produced and tested for binding. We observed binding three-fold above background for antibody H11.A3.2 with either clone. Binding of HPV 6-specific antibodies H6.B 10.5 and H6.M48 was not perturbed by clone 1393:6:169–178, demonstrating that these VLPs retained HPV 6-like character. Work described in this document demonstrates that HPV 6-specific antibodies target region 49–54, therefore it is expected that VLPs produced from clone 1393:6:49–54 will not bind these antibodies. The binding of HPV 11-specific antibody H11.B2, known to bind elsewhere, was not observed, thus demonstrating that the transfer was specific to H11.A3.2.

EXAMPLE 9

Monitoring Serological Responses to HPV 11 Infection or Immunization

HPV 6-modified VLPs are used to determine the presence of an immune response to HPV 11 following viral infection or immunization with HPV 11 VLPs. HPV 6-modified VLPs which present the HPV 11 neutralizing epitope to H11.G3 and/or H11.H3 are coated onto the well of a microtitre plate in native form. Following blocking, HPV 11 monoclonal antibody H11.G3 and/or H11.H3 is incubated in ELISA format with increasing amounts of HPV 11 polyclonal sera, HPV 6 polyclonal sera, and test polyclonal sera. Binding of the HPV 11 monoclonal antibody is visualized using a rabbit anti-mouse IgG secondary antibody. Alternatively, it is labeled with $I^{125}$, or coupled directly to horseradish peroxidase or alkaline phosphatase, or another standard ELISA visualization protocol. An increasing amount of polyclonal HPV 11 sera competes with binding until the signal eventually is reduced to background level. Polyclonal HPV 6 sera does not compete, or the competition is significantly reduced from that observed with HPV 11 polyclonal sera. Competition with the test sera at levels comparable to HPV 11 polyclonal sera demonstrates an immune response to HPV 11. Lack of, or a significant reduction of competition demonstrates lack of or a weak immune response to HPV 11.

EXAMPLE 10

Monitoring Serological Responses to HPV 6 Infection or Immunization

HPV 11-modified VLPs are used to determine the presence of an immune response to HPV 6 following viral infection or immunization with HPV 6 VLPs. HPV 11 modified VLPs which present the HPV 6 epitope to H6.N8 and/or H6.M48 are coated onto the well of a microtitre plate in native form. Following blocking, HPV 6 monoclonal antibody H6.N8 and/or H6.M48 is incubated in ELISA format with increasing amounts of HPV 11 polyclonal sera, HPV 6 polyclonal sera, and test polyclonal sera. Binding of the HPV 6 monoclonal antibodies H6.N8 and/or H6.M48 is visualized using a rabbit anti-mouse IgG secondary antibody. Alternatively, they are labeled with $I^{125}$, or coupled directly to horseradish peroxidase or alkaline phosphatase, or another standard ELISA visualization protocol. Increasing amounts of polyclonal HPV 6 sera should compete with binding until the signal eventually is reduced to background level. Polyclonal HPV 11 sera does not compete. Competition with the test sera at levels comparable to HPV 6 polyclonal sera demonstrates an immune response to HPV 6. Lack of or significant reduction of competition demonstrates lack of or a weak immune response to HPV 11.

EXAMPLE 11

Generation of Chimeric VLPs Which Stimulate Both Type 6 and Type 11 Specific Responses HPV 6 VLPs modified to contain substitutions, S131G and Y132, T345S, T346S, and S348A, produce VLPs which present i) the HPV 6-specific and VLP dependent epitope and ii) all known HPV 11 specific and neutralizing epitopes. Alternatively, HPV 11 VLPs modified to contain substitution K53R, or Y49F and K53R, or Y49F, K53R, V54A, T170K, S173T, S 176P, N179A produce VLPs which present i) the HPV 6-specific and VLP dependent epitope and ii) the major HPV 11 specific and neutralizing epitopes. These latter chimeric VLPs present the one type 6 specific epitope known, the two neutralizing type 11 epitopes known, and the 6/11 common epitopes. Chimeric 6/11 VLPs are able to replace double immunization with type 6 and type 11 VLPs to stimulate immune responses, with reduced productivity costs.

What is claimed is:

1. A recombinant HPV 6 L1 protein which comprises an HPV 11 conformational epitope, the HPV6 protein comprising a mutation at locations selected from the group consisting of:

(i) K169, T172, P175, and A178;

(ii) T345, T346, and S348;

(iii) F49, R53, and A54; and (iv) E262, T270, S276, G277, T280, G283 and N289.

2. A HPV 6 protein according to claim 1 which comprises a mutation at locations selected from the group consisting of:

(i) K169T, T172S, P175S, and A178N;

(ii) T345S, T346K, and S348A;

(iii) F49Y, R53K, and A54V; and (iv) E262T, T270D, S276G, G277N, T280S, G283A and N289H.

* * * * *